US012644117B2

(12) United States Patent
Abdul Rahman

(10) Patent No.: US 12,644,117 B2
(45) Date of Patent: Jun. 2, 2026

(54) METHOD OF ENABLING POOLED-LIBRARY BASED NUCLEIC ACID CONSTRUCTS SCREENING

(71) Applicant: LEADXPRO AG, Villigen (CH)

(72) Inventor: Wassim Maxime Abdul Rahman, Saint-Louis (FR)

(73) Assignee: LEADXPRO AG, Villigen (CH)

( * ) Notice: Subject to any disclaimer, the term of this patent is extended or adjusted under 35 U.S.C. 154(b) by 1051 days.

(21) Appl. No.: 17/756,162

(22) PCT Filed: Nov. 19, 2020

(86) PCT No.: PCT/EP2020/082720
§ 371 (c)(1),
(2) Date: May 18, 2022

(87) PCT Pub. No.: WO2021/099483
PCT Pub. Date: May 27, 2021

(65) Prior Publication Data
US 2022/0411788 A1      Dec. 29, 2022

(30) Foreign Application Priority Data
Nov. 20, 2019    (EP) .................................... 19210343

(51) Int. Cl.
*C12N 15/10* (2006.01)
*C12N 5/07* (2010.01)
*C12N 15/86* (2006.01)

(52) U.S. Cl.
CPC ....... *C12N 15/1082* (2013.01); *C12N 5/0601* (2013.01); *C12N 15/1086* (2013.01); *C12N 15/86* (2013.01); *C12N 2710/14043* (2013.01)

(58) Field of Classification Search
CPC .............. A61K 31/4706; C12N 5/0601; C12N 15/1034; C12N 15/1082; C12N 15/1086; C12N 15/1093; C12N 15/86; C12N 2710/14043; C40B 40/02; C40B 40/08
See application file for complete search history.

(56) References Cited

FOREIGN PATENT DOCUMENTS

WO        02/072814 A2      9/2002

OTHER PUBLICATIONS

Ernst et al., "Baculovirus Surface Display: Construction and Screening of a Eukaryotic Epitope Library," Nucleic Acids Research 26(7): 1718-1723 (1998).
Sanz et al., "Chloroquine-Enhanced Gene Delivery Mediated by Carbon Nanotubes," Carbon 49: 5348-5358 (2011).
Volkman et al., "Mechanism of Neutralization of Budded *Autographa californica* Nuclear Polyhedrosis Virus by a Monoclonal Antibody: Inhibition of Entry by Adsorptive Endocytosis," Virology 143:185-195 (1985).
Wang et al., "Using a Baculovirus Display Library to Identify MHC Class 1 Mimotopes," PNAS 102(7):2476-2481 (2005).
Xu et al., "Baculovirus Superinfection: A Probable Restriction Factor on the Surface Display of Proteins for Library Screening," PLOS One 8(1):e54631 , pp. 1-8 (2013).
The International Search Report issued in PCT/EP2020/082720 mailed Feb. 19, 2021.
Farias, et al., "Effect of ammonium chloride on the multiplication of infectious pancreatic necrosis virus," *Arch. Virol.* 98(3-4):155-162 (1988).
Jefferson, et al., "Neuraminidase inhibitors for preventing and treating influenza in adults and children", *Cochrane Database Syst Rev.* 4:CD008965 (2014).

*Primary Examiner* — Jeremy C Flinders
(74) *Attorney, Agent, or Firm* — MEDLER FERRO WOODHOUSE & MILLS PLLC

(57) ABSTRACT

The invention relates to a method for generating in a single step a library of recombinant baculoviruses for screening for a protein of interest, starting from a pooled-library of poly-nucleotides each encoding a different protein. Insect cells are infected with a pooled-library of baculoviruses at a very low multiplicity of infection (MOI) leading to the situation where the majority of cells are infected by a single baculovirus. The pool of cells is then treated with a viral inhibitor which prevents secreted baculoviruses from penetrating other cells without affecting, either the capacity of the cell to express the target protein, nor intracellular viral replication and accumulation.

16 Claims, 3 Drawing Sheets

Chloroquine

METHOD OF ENABLING POOLED-LIBRARY BASED NUCLEIC ACID CONSTRUCTS SCREENING

RELATED ART

Identification of gene function is a critical step in the selection of new molecular targets for drug discovery, gene therapy, clinical diagnostics, agrochemical discovery, engineering of transgenic plants, e g, with novel resistance traits or enhanced nutritional characteristics, and genetic engineering of prokaryotes and higher organisms for the production of industrial chemicals, biochemicals, and chemical intermediates. Historically, library screening methods have been used to screen large numbers of uncharacterized genes to identify a gene or genes associated with a particular phenotype, e.g., hybridization screening of nucleic acid libraries, antibody screening of expression libraries, and phenotypic screening of libraries.

Over the past few years, many organisms have had their genomes completely sequenced. A draft sequence of the entire human genome has been published. However, sequence information as such does not explain what all the genes do, how cells work, how cells form organisms, what goes wrong in disease, how we age or how to develop a drug. This is where functional genomics, an area of the post-genomic era that deals with the functional analysis of genes and their products comes into play.

Among the techniques of functional genomics, both DNA microarrays and proteomics hold great promise for the study of complex biological systems. Proteomics (the complete set of proteins encoded by a cell at any one time) addresses problems that cannot be approached by DNA analysis, namely, relative abundance of the protein product, post-translational modification, subcellular localization, turnover, interaction with other proteins as well as functional aspects.

Structural and biochemical characterization of proteins is limited as it is difficult to produce a sufficient amount of the desired protein and of a high enough quality to enable characterization. Directed evolution has been shown to be helpful for optimizing expression of proteins in *E. coli* (Sarkar et al. PNAS, 2008, Vol. 105 (39) and Dodevski & Plückthun, 2011, J Mol Biol 408:599-615). Nevertheless *E. coli* is lacking most of the post-translational modifications (PTMs) which are often essential for the folding and expression of the target protein. The Baculovirus Expression Vector System (BVEVS) has widely been shown to be effective for expressing human proteins in insect cells in sufficient amounts for structural studies. For example, BVEVS is by far the most commonly used system for the expression of GPCRs for structural studies (GPCRdb).

In addition, insect cells infected with recombinant baculovirus execute most of the human post translational modifications leading to a high molecular fidelity level, a prerequisite to structure-based drug design on human protein targets.

The ideal eukaryotic host to develop a system for increasing protein expression would be BVEVS, however, insect cells can't be individually transduced with constructs from a pooled-library, which is the essential condition to any pooled-library based screening approach. This is due to BVEV's spreading (multiple BVEVs transduce one insect cell). In fact between 10-12 hours after a baculovirus expressing the protein of interest penetrates an insect cell, the virus starts spreading in the extracellular media and penetrates other cells, this leads to cells transduced with several baculoviruses. If insect cells are transduced with a pooled-library of baculoviruses each expressing a different variant of the protein of interest, the baculovirus constructs will spread via the extracellular media to infect other insect cells, leading to different variants of the protein of interest in one insect cell. For this reason, past efforts to develop a pooled-library based screening approach were only focused on expression systems such as *E. coli* (EP2802656B 1) or *Saccharomyces cerevisae* (US20180003711A1). In these systems it's technically simple to transform a cell with a single plasmid.

Baculoviruses have long been used as biopesticides and as tools for efficient recombinant protein production in insect cells. They are generally regarded as safe, due to their naturally high species-specificity and because they are not known to propagate in any non-invertebrate host.

There are methods disclosed in the art which rely on the generation of proteins or polypeptides from genes collections and in particular use high thorough put screening where each gene is analyzed in an individual compartment. However, one major disadvantage with such methods is that the proteins or polypeptides are generated individually from each gene. There is a need for screening methods, such as pooled based screening, which allow for rapid identification of individual proteins or polypeptides, and which in turn will also allow for identification of genes coding for such proteins or polypeptides.

SUMMARY OF THE INVENTION

The invention relates to a surprising method for generating in a single step a library of recombinant baculoviruses for screening for a protein of interest, starting from a pooled-library of poly-nucleotides each encoding a different protein. Insect cells are infected with a pooled-library of baculoviruses at a very low multiplicity of infection (MOI) leading to the situation where the majority of cells are infected by a single baculovirus. The pool of cells is then treated with a viral inhibitor which prevents secreted baculoviruses from penetrating other cells without affecting, either the capacity of the cell to express the target protein, nor intracellular viral replication and accumulation.

A pool of cells, each infected with a baculovirus which corresponds to a unique target protein is generated. The capacity of each cell to express the target protein is analyzed. Individual cells expressing the target protein at a high level are isolated and mixed with other insect cells in the absence of viral inhibitors, thus allowing virus spreading and amplification to reach a virus concentration compatible with sequencing of the virus and identification of protein with high expression levels.

Therefore, in an aspect, the present invention provides a method for screening proteins and polypeptides to identify a protein or polypeptide of interest, which comprises the sequential steps of:

(i) generating a pooled-library of genes or genomic fragments cloned in baculovirus as a vector, (ii) transducing host cells with the pooled-library of baculovirus vectors, at a multiplicity of infection (MOI) between 0.1-0.01, (iii) washing the host cells 2-4 hours post infection in a washing step, (iv) adding a viral inhibitor to the host cells, (v) culturing the cells for at least 2 days, preferably between 2 to 5 days, so that the protein of interest is expressed in the host cells, wherein the viral inhibitor inhibits viral infection of the host cell and does not inhibit the ability of the host cell to produce the protein of interest.

In another aspect, the invention relates a viral inhibitor for use in protein screening.

In another aspect, the invention relates to a viral inhibitor for use in gene therapy.

These and further aspects and preferred embodiments thereof are also additionally defined below in the detailed description and in the claims.

These methods and uses would find widespread use in academic laboratories, pharmaceutical companies, genomics companies, agricultural companies, chemical companies, and in the biotechnology industry.

DETAILED DESCRIPTION OF THE INVENTION

Figure 1:
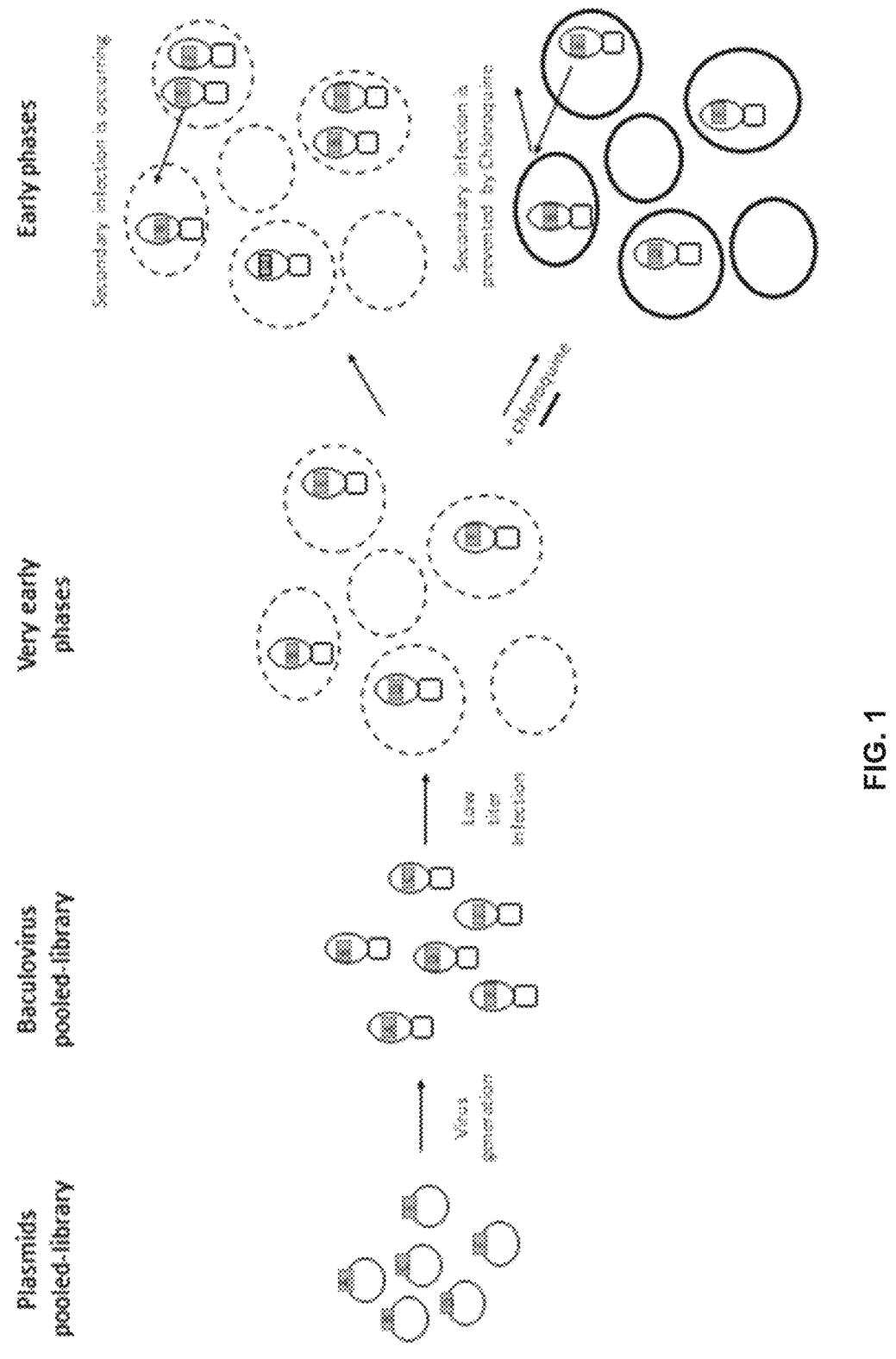
FIG. 1: Diagram demonstrating BVEV library construction with and without chloroquine treatment.

A pooled-library of poly-nucleotides each corresponding to a variant of the target protein or an array of different proteins, is used to generate a library of recombinant baculoviruses. The system used for generating recombinant baculovirus described in Zhao et al., Nucleic Acid Research, 2003, Vol 31, No. 2 is used to generate recombinant baculoviruses starting from poly-nucleotides encoding for one variant of the protein of interest or an array of different proteins, unlike our approach which consists on generating with a single step recombinant baculoviruses starting from a pooled-library of poly-nucleotides each encoding for a different protein variant or an array of different proteins (FIG. 1). Once the pool of viruses is generated it is used to infect insect cells at a very low Multiplicity of infection (MOI), preferably lower than 0.1, which means that for every 10 cells only one virus will be added. Multiplicity of infection is the number of virus particles added per cell, for this the viral titer and cell number is calculated using standard methods. In these conditions the probability that a single cell is infected by several baculoviruses is very low, leading to cells expressing each a different protein. Insect cells infected with baculovirus replicate the virus and 10 to 12 hours after infection, before reaching a detectable expression level, the virus begins to spread into the extracellular media (FIG. 1). The virus is then able to infect other cells, which will lead to a situation where insect cells are infected by several baculoviruses, each corresponding to a different variant of the protein of interest.

In the presence of viral inhibitors (SPINS), baculoviruses released into the extracellular media are unable to infect other insect cells. Herein the term SPINs is defined as a viral inhibitor that prevents BVEVs from penetrating cells after their cellular secretion, thus preventing virus spreading, and wherein the viral inhibitor does not affect the quality or quantity of the protein of interest that is produced by the cells. SPINS do not affect the capacity of the cell to express the target protein and to replicate the recombinant baculovirus (FIG. 1). SPINS do not affect intracellular viral replication and accumulation. This transforms cells into individual compartments expressing the same variant of the protein of interest. An example of viral inhibitor SPINS is Chloroquine which has a known effect in preventing Baculovirus spreading by preventing release of baculoviruses from endosomes (Volkman 1986, Volkman & Goldsmith 1985).

The aim of this invention is to generate a system which is compatible with protein variants or an array of different proteins scanning in a library approach. The different proteins are screened according to their capacity to express functional protein at a high level. High-score cells are isolated and collected in a small cells culture dish pre-seeded with insect cells in the absence of viral inhibitor SPINS. In these conditions virus can infect other cells and is amplified to a high level, allowing sequencing of the virus expressing the hit variant. For example selected hit variants are can be expressed in a scale compatible with structural studies.

Unless defined otherwise, all technical and scientific terms used herein have the same meanings as commonly understood by one of ordinary skill in the art to which this invention belongs. The herein described and disclosed embodiments, preferred embodiments and very preferred embodiments should apply to all aspects and other embodiments, preferred embodiments and very preferred embodiments irrespective of whether it is specifically again referred to or its repetition is avoided for the sake of conciseness. The articles "a" and "an", as used herein, refer to one or to more than one (i.e., to at least one) of the grammatical object of the article. The term "or", as used herein, should be understood to mean "and/or", unless the context clearly indicates otherwise.

In an aspect, the present invention provides a method for screening proteins and polypeptides to identify a protein or polypeptide of interest, which comprises the sequential steps of:

(i) generating a pooled-library of genes or genomic fragments cloned in baculovirus as a vector, (ii) transducing host cells with the pooled-library of baculovirus vectors at a multiplicity of infection (MOI) of 0.1-0.01, (iii) washing the host cells 2-4 hours post infection in a washing step, (iv) adding a viral inhibitor to the host cells, (v) culturing the cells for at least 2 days, preferably between 2 to 5 days, so that the protein of interest is expressed in the host cells, wherein the viral inhibitor inhibits viral infection of the host cell and does not inhibit the ability of the host cell to produce the protein of interest.

The viral inhibitor inhibits viral infection, means the partial, preferably the complete prevention of viral infection. The ability to inhibit viral infection is measured relative to viral infection in the absence of the viral inhibitor.

The ability of the host cell to produce the protein of interest is measured relative to the host cell's ability to produce the protein in the absence of the viral inhibitor.

Baculoviruses are large enveloped insect viruses. The cigar-shaped nucleocapsid of the baculovirus encloses a 134 kb sized DNA genome. Baculoviruses exist in two forms during natural infection. An occlusion derived virus, ODV, transmits infection from host to host and a budded virus, BV, spreads the infection within the host.

The baculovirus *Autographa californica* multicapsid nuclepolyhedrovirus (AcMNPV) has many features that make it a promising new tool for gene therapy. Baculoviruses have very restricted host range and they do not replicate in vertebrate cells, yet AcMNPV, having a eukaryotic promoter, can effectively transduce mammalian cells. Baculovirus-derived vectors can carry over 50 kb of foreign DNA in their genome, which enables a delivery of complex constructs into target cells. The *Autographa californica* multiple nuclear polyhedrosis virus (AcMNPV), containing an appropriate eukaryotic promoter, is able to efficiently transfer and express target genes in several mammalian cell types in vitro. The ease of manipulation and rapid construction of recombinant baculoviruses, the lack of cytotoxicity in mammalian cells, even at a high multiplicity of infection, an inherent incapability to replicate in mammalian cells, and a large capacity for the insertion of foreign sequences, are features of baculovirus. In one embodiment the Baculovirus is *Autographa californica* multicapsid nuclepolyhedrovirus or *Bombyx mori* nuclear polyhedrosis virus. In a preferred embodiment the Baculovirus is baculovirus *Autographa californica* multicapsid nuclepolyhedrovirus.

Baculoviral genomic or cDNA libraries offer a powerful tool for phenomics, by enabling the functional screening of the constructed libraries in eukaryotic cells both in vitro and in vivo. Addition of a bacterial promoter into a baculovirus donor vector will also allow expression screening of cDNA libraries in bacterial cells. Baculovirus libraries may be constructed from suitable validated full-length clones and sequences from human and other vertebrate sources. This will allow integration of the efficient infection and transduction of target cells by baculoviruses, and application to phenomics. A pooled-library of baculovirus is a plurality of baculovirus each having at least one target polynucleotide. The term "pooled" as used herein means "combined". Further the term "pooled-library of baculovius" means all baculovirus are in the same container.

The constructed expression cassette may be cloned into any suitable baculovirus plasmid or baculovirus system which can act as a donor vector. pBACPAK8 is a preferred plasmid. The preferred method for generating the baculovius plasmid is described in Zhao et al., Nucleic Acid Research, 2003, Vol 31, No. 2. This system relies on the use of baculoviruses with Knocked out ORF1629. The plasmid carrying the gene of interest also contains a wild type copy of ORF1629. After recombination in insect cells the ORF1629 is rescued, meaning that only recombinant baculovirus have a functional ORF1629 and can replicate. Examples of baculovirus expression vectors include Flashbac (by OET), Baculogold (by BD) or BestBac 2.0 (by expression systems).

A pooled-library of genes or genomic fragments is a plurality of polynucleotide variants each having at least one defined nucleotide difference relative to a reference polynucleotide sequence or an array of different proteins. In one embodiment the library comprises at least 10 polynucleotide variants, in a preferred embodiment at least one of the polynucleotide variants comprises at least two defined nucleotide differences relative to the reference polynucleotide sequence. In a more preferred embodiment the reference polynucleotide encodes a reference polypeptide and each of the plurality of polynucleotide variants encodes a polypeptide having at least one defined amino acid sequence difference as compared to the reference polypeptide. In a more preferred embodiment the library comprises a polynucleotide variant encoding a polypeptide with an improvement in a desired property of a reference polypeptide encoded by the reference polynucleotide. In another embodiment the pooled library of genes or genomic fragments are large libraries of polynucleotide variant sequences having defined nucleotide differences (e.g., libraries of 10, 50, 100, 150, or more variants, each having 1, 2, 3, 5, 9, 12, 15, or more, desired changes), with relatively few (e.g., compared to whole gene synthesis methods), and relatively short (e.g., 35-mer or less) oligonucleotides. "Library" refers to a set (e.g., a plurality) of heterogeneous polypeptides or nucleic acids. A library is composed of members, which have a single polypeptide or nucleic acid sequence. To this extent, "library" is synonymous with "repertoire". Sequence differences between library members are responsible for the diversity present in the library. The library may take the form of a simple mixture of polypeptides or nucleic acids, or may be in the form organisms or cells, for example bacteria, viruses, animal or plant cells and the like, transformed with a library of nucleic acids. The term "pooled" as used herein means "combined". Further the term "pooled nucleotides" means all poly nucleotides are in the same container.

When a viral vector or viral particle is used to transfer genetic material of interest into a cell, the technique is referred to as "transduction". Thus generally, to "transduce" a cell is to use a viral vector or viral particle to transfer genetic material into a cell.

The term "infection" refers to the invasion by pathogenic viral agents of cells where conditions are favorable for their replication. Such invasion can occur by placing the viral particles directly on the insect cell culture or by injection of the insect larvae with the recombinant virus or by oral ingestion of the viral particles by the insect.

In another embodiment the pooled-library of genes or genomic fragments cloned in baculovirus as a vector, include detectable markers. Detectable markers are genes which allow detection of cells that have been transfected or transduced with the gene. Detectable markers include reporter genes and selection genes. Reporter genes are genes which confer a characteristic onto the cell which is detectable. Suitable reporter genes include the gene encoding for green fluorescent protein, the β-galactosidase gene and the chloramphenicol acetyl transferase gene. Selection genes are wild-type alleles of genes that encode for enzymes which allow the cell to grow on certain media, such as media containing antibiotics. These genes include, for example, the prokaryotic hygromycin resistance and neomycin resistance genes.

In the context of the present invention, the term "proteins or polypeptides" means that the proteins or polypeptides expressed from the gene library are individually identifiable, rather than forming part of a pool. Thus, for instance, the proteins or polypeptides can be expressed as an array wherein each protein or polypeptide occupies a distinct point or area within the array. For example, a gene library may be generated in the form of colonies or plaques, which in turn can be picked off individually and arranged in an array. Expression of the genes will in turn result in an array of proteins or polypeptides in an array format, each occupying a distinct point or area.

The proteins or polypeptides generated from the gene libraries may be termed "synthetic proteins or polypeptides" produced by in vitro methods such as in vitro transcription and translation, ribosome display and phage display. Thus, they may be distinguished on that basis from "natural proteins" derived directly from tissue or cell extracts. The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

Thus, the methods described herein allow for screening of proteins and polypeptides and post-translational modifications using gene libraries as the starting point for synthesis of "synthetic" proteins or polypeptides. In general this is achieved by the generation of arrays of proteins or polypeptides as a means for screening them. In particular, the arrays are generated by in vitro transcription and translation methods.

A common theme of the present invention is that the methods provided each permit the rapid identification of a "synthetic" protein or polypeptide by virtue of its corresponding mRNA or gene sequence.

Within the method of the present invention, it will be apparent to those skilled in the art that various measures could be used to optimize the folding and stability of protein molecules especially from degradation by proteases. For correct protein folding, optimal oxidative protein folding conditions would be used in translation reactions with particular measures to optimize disulphide bond formation through, for example, use of molecular chaperones such as protein disulphide isomerase. Once the final polypeptide/ribosome/mRNA complexes are formed, it may be beneficial to stabilize these complexes using standard translational inhibitors such as chloramphenicol.

It will be obvious for the present invention that a prime application will be in the analysis of proteins, protein modifications and protein-protein interactions which relate to human disease or to the healthcare, individual or drug treatment status of humans.

In another embodiment, the method further comprises the step vi) identifying and isolating the protein of interest. As used herein, "isolated" means separated from one or more other compounds or entities, e.g., entities with which it is otherwise found. The term "isolated" may be used interchangeably with the term "purified". A compound or entity may be partially purified, substantially purified, or pure, where it is pure when it is removed from substantially all other compounds or entities, i.e., is preferably at least about 90%, more preferably at least about 91%, 92%, 93%, 94%, 95%, 96%, 97%, 98%, 99%, or greater than 99% pure. For example, when a protein is expressed in a cell, it will be considered purified when it is removed from one or more, preferably most, other cellular components, such as other proteins expressed by the cell. In a more preferred embodiment, the method further comprises a step vi) identifying and isolating the gene corresponding to the protein of interest. In another embodiment the method comprises a further step vi) wherein the host cell with the protein of interest is cultivated in the absence of viral inhibitor, to quantities that are compatible with gene sequencing.

In a preferred embodiment the protein of interest is identified by a selected phenotype. In a more preferred embodiment the protein of interest is assayed for the selected phenotype using flow cytometry. In a preferred embodiment the proteins are screened according to their capacity to express functional protein at a high level. A high level herein would be defined as a level which is compatible with structural studies or biophysical assays. In another embodiment the term high level may mean greater than 0.5 mg of pure protein from 1 million cells, or greater than 1 mg of pure protein from 1 million cells or greater than 1.5 mg of pure protein from 1 million cells or greater than 2 mg of pure protein from 1 million cells. A functional protein includes a correctly folded protein. A correctly folded protein is for example a protein that is capable of binding to a natural ligand. As used herein, the term "fold" is therefore taken in its broadest context to mean a tertiary structure formed by the folding of multiple secondary structures including aspects of both architecture and topology. Herein, the term "subdomain" is used interchangeably with the term "fold". A "fold" may form independently or in association with other parts of a protein or other proteins or a scaffold structure.

A "selected phenotype" refers to any phenotype, e.g., any observable characteristic such as a physical, chemical, or functional effect that can be measured in an assay such as changes in cell growth, proliferation, morphology, enzyme function, signal transduction, expression patterns, downstream expression patterns, reporter gene activation, hormone release, growth factor release, neurotransmitter release, ligand binding, apoptosis, and product formation. Such assays include, e.g., transformation assays, e.g., changes in proliferation, anchorage dependence, growth factor dependence, foci formation, and growth in soft agar; apoptosis assays, e.g., DNA laddering and cell death, expression of genes involved in apoptosis; signal transduction assays, e.g., changes in intracellular calcium, cAMP, cGMP, IP3, changes in hormone and neurotransmitter release; receptor assays, e.g., estrogen receptor and cell growth; growth factor assays, e.g., EPO, hypoxia and erythrocyte colony forming units assays; enzyme production assays, e.g., FAD-2 induced oil desaturation; pathogen resistance assays, e.g., insect, bacterial, and viral resistance assays; chemical production assays, e.g., penicillin production; transcription assays, e.g., reporter gene assays; and protein production assays, e.g., VEGF ELISAs.

In a more preferred embodiment the method comprises a further step vii) identification and isolation of genes associated with a selected phenotype. After assaying for phenotypic changes, as described above, those cells exhibiting an altered phenotype are selected for further study, in which the genes associated with the change in phenotype are identified and isolated.

In another embodiment, the host cell is an insect cell or a bacterial cell. In a more preferred embodiment the host cell is an insect cell. In an even more preferred embodiment the insect cell is the insect cell line Sf9 (*Spodoptera Frugiperda*).

The term "insect cells" means insect cells from the insect species which are subject to baculovirus infection. For example, without limitation: *Autographa californica; Bombyx mori; Spodoptera frugiperda; Choristoneura fumiferana; Heliothis virescens; Heliothis zea; Helicoverpa zea; Helicoverpa virescens; Orgyia pseudotsugata; Lymantria dispar; Plutella xylostella*; Malacostoma disstria; *Trichoplusia ni; Pieris rapae; Mamestra* configurata; *Mamestra brassica*; Hyalophora cecropia.

In another embodiment, the host cells are pooled together and transduced in a batch.

In another embodiment, the viral inhibitors inhibition of viral infection is reversible. The term "reversible" means the ability to return to the original or prior state or condition.

In a preferred embodiment the viral inhibitor does not inhibit viral replication. "Replication" means the process of production of a new DNA strand using a DNA template strand for the copying of the information content of the genome. A baculovirus chromosome which is capable of replication is capable of initiating the reproduction of its genome in the host cell.

In another embodiment, the viral inhibitor does not affect production of the proteins and polypeptides. To not affect the production of the proteins and polypeptides would mean to not affect the level of protein or polypeptide concentration compared to a method that does not use a viral inhibitor.

In another embodiment, the viral inhibitor does not affect intracellular viral replication and accumulation. In another embodiment, the viral inhibitor does not affect the capacity of the host cell to express the protein of interest. In preferred embodiment, the viral inhibitor does not affect the post translation modification of the protein of interest. In a more preferred embodiment the viral inhibitor does not affect the folding and molecular fidelity of the protein. In a more preferred embodiment the high molecular fidelity of the protein of interest is not affected by the presence of the viral inhibitor. High molecular fidelity means the capacity of the heterologous system to express a target protein with exactly the same structure and function as in the original system. For example, a human protein expressed in insect cells has high molecular fidelity if the post translational modifications of this protein in insect cells are the same as when it is expressed in the original human cells.

In a more preferred embodiment, the viral inhibitor is chloroquine, ammonium chloride, Tamiflu, Neuraminidae. In a more preferred embodiment the viral inhibitor is chloroquine and ammonimum chloride. In an even more preferred embodiment the viral inhibitor is chloroquine.

In another embodiment, the viral inhibitor is added at a concentration in the range of 0.1 mM-1 mM, or 0.05 mM-1 mM, or 0.1 mM-0.9 mM, or 0.2 mM-0.8 mM, or 0.1 mM-0.8 mM, or 0.1 mM-2 mM, or 0.5 mM-1.5 mM, or 0.5 mM-4 mM.

In a preferred embodiment, the viral inhibitor is chloroquine and the chloroquine is added at a concentration of between 0.1 mM and 2 mM.

In another embodiment, the protein of interest is identified using flow cytometry.

Encompassed by the present invention are also methods where synthetic proteins generated from gene libraries are subjected to protein gel electrophoresis for the analysis of protein modification or protein-protein binding.

In another embodiment, the host cells are cultured to expand cells to levels of protein or polypeptide required for screening and/or analysis.

These assays can be in vitro, in vivo, and ex vivo. Functional effects can be measured by any means known to those skilled in the art, e.g., measurement of RNA or protein levels, measurement of RNA stability, identification of downstream or reporter gene expression, e.g., via chemiluminescence, fluorescence, fluorescent activated cell sorting ("FACS"), colorimetric reactions, antibody binding, inducible markers, ligand binding assays; changes in intracellular second messengers such as cGMP and inositol triphosphate (IP3); changes in intracellular calcium levels; cytokine release, and the like, as described herein.

In another aspect the present invention provides, a viral inhibitor for use in protein screening. In another embodiment the viral inhibitor is chloroquine, ammonium chloride, Tamiflu, Neuraminidae. In another embodiment the viral inhibitor is used to inhibit a viral vector from infecting more than one cell.

In another aspect the present invention provides, a viral inhibitor for use in gene therapy. In another embodiment the viral inhibitor is chloroquine, ammonium chloride, Tamiflu, Neuraminidae. In another embodiment the viral inhibitor is used to inhibit a viral vector from infecting more than one cell.

EXAMPLES

Example 1

Chloroquine, one of the known SPINS, was used to demonstrate the capacity of these molecules to prevent baculovirus spreading, without affecting the capacity of cells to express the target protein.

A recombinant ACMNPV baculovirus was generated by homologous recombination and expressed a target fluorescent protein. The fluorescent protein was the Yellow Fluorescent Protein (YFP) from the organism *Aequorea Victoria*.

Three hours before infection 0.5 million Sf9 insect cells (ThermoFisher) were seeded into two wells of a 6 well-plate (ThermoFisher). Sf9 cells are cultivated in sf900 II media (ThermoFisher).

The initial viral stock titer was estimated to be approximately 1 million baculoviruses per milliliter. The recombinant baculovirus was added to the cells to reach a MOI of approximately 0.02. The added virus volume per well was 10 micolitre. The virus was resuspended in sf900 II media (ThermoFisher).

Cells were incubated in a 27° C. incubator. Four hours after infection, attached cells are washed with PBS to remove baculoviruses which have not penetrated into cells. The wash consisted of three times with 1 ml per cell of PBS media.

Chloroquine diphosphate salt (CC6628 from Sigma) was added to a final concentration of 0.8 mM. In the control condition insect cell media without chloroquine was added to the cells. Cells were incubated in a 27° C. incubator.

Figure 2A:
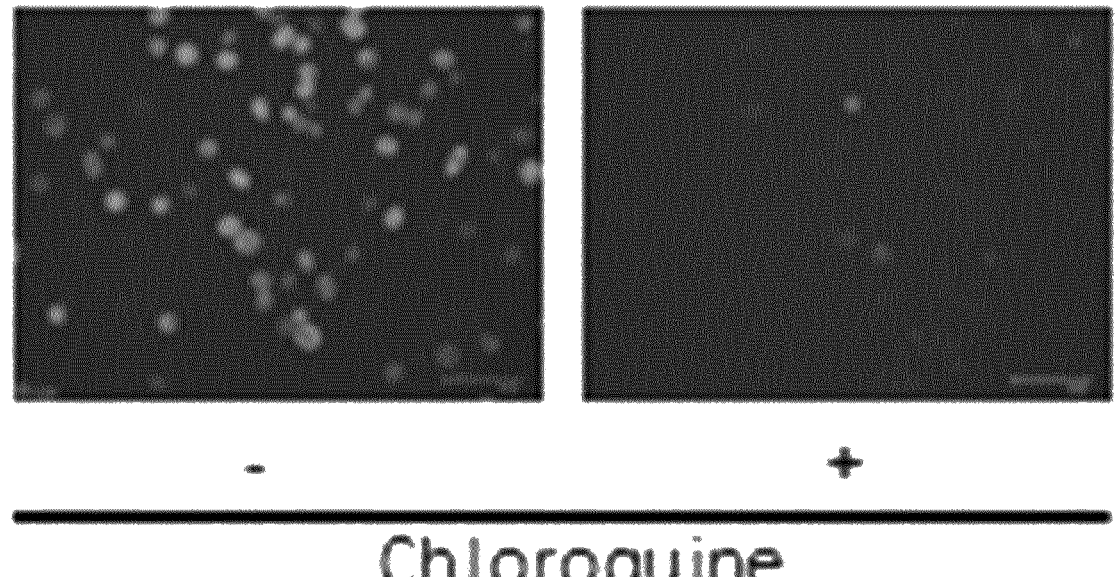
FIG. 2A: Fluorescence microscopy images two days after SD insect cells are infected with baculovirus with a fluorescent protein. Cells were transduced at an MOI of approximately 0.02 and treated with and without chloroquine.

Fluorescence microscopy was performed 2 days after infection (FIG. 2A). The results demonstrate a relatively low proportion of fluorescent cells in the presence of chloroquine (around 1%) and a considerably higher proportion of fluorescent cells in the absence of chloroquine (around 10%).

Figure 2B:
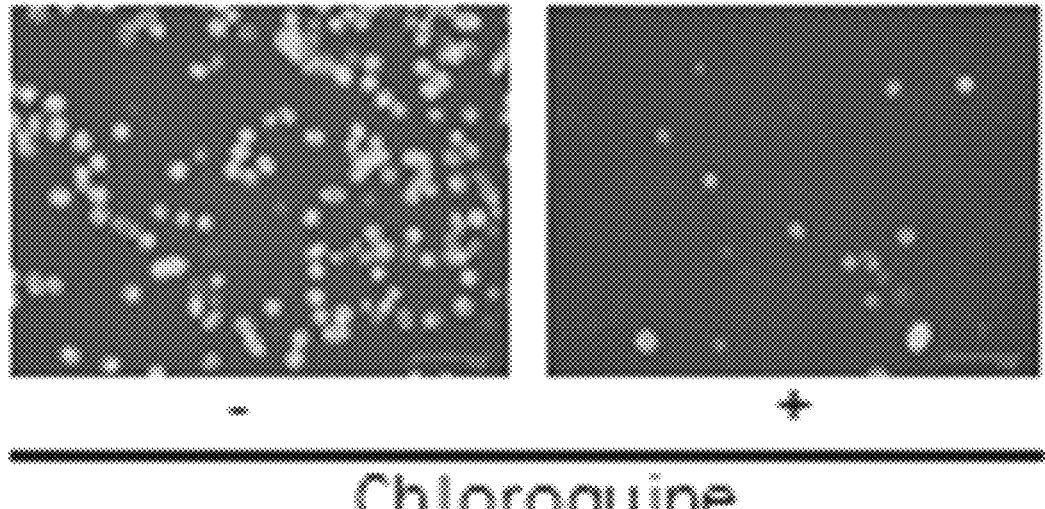
FIG. 2B: Fluorescence microscopy images five days post infection of SD insect cells treated with and without chloroquine.

Five days after infection, in the absence of Chloroquine, the proportion of fluorescent cells significantly increased indicating continuous baculovirus replication and spreading in the culture (FIG. 2B). In the presence of chloroquine, the proportion of fluorescent cells is constant despite an increase of fluorescence intensity by cell (FIG. 2B), indicating accumulation of expressed YFP protein and virus without increasing the number of infected cells. The cells showing an increase in fluorescent intensity demonstrates an increase in the number of target proteins expressed and also indicates that the protein produced is of a high quality, as the YFP would not fluoresce without the correct expression and folding pattern of the protein. The results suggest the cells treated with Chloroquine were infected with one baculovirus corresponding to one target protein. In addition the virus produced high quality protein correctly folded within the individual cells.

The invention claimed is:

1. A method for screening proteins and polypeptides to identify a protein or polypeptide of interest, which comprises the sequential steps of:

i) generating a pooled-library of genes or genomic fragments cloned in baculovirus as a vector, (ii) transducing host cells with the pooled-library of baculovirus vectors at a multiplicity of infection (MOI) of less than 0.1, (iii) washing the host cells 2-4 hours post infection in a washing step, (iv) adding a viral inhibitor to the host cells, (v) culturing the cells for at least 2 days, so that the protein of interest is expressed in the host cells, wherein the viral inhibitor is selected from the group consisting of chloroquine, ammonium chloride, oseltamivir, or a neuraminidase inhibitor.

2. The method of claim 1, further comprising step (vi) identifying and isolating the protein of interest.

3. The method of claim 1, wherein the host cell is an insect cell.

4. The method of claim 1, wherein the host cells are pooled together and transduced in a batch.

5. The method of claim 1, wherein the viral inhibitor's inhibition of viral infection is reversible.

6. The method of claim 1, wherein the viral inhibitor does not affect production of the proteins and polypeptides.

7. The method of claim 1, wherein the viral inhibitor is chloroquine.

8. The method of claim 7, wherein the chloroquine is added at a concentration of between 0.1 mM and 2 mM.

9. The method of claim 1, wherein the protein of interest is identified using flow cytometry.

10. The method of claim 1, wherein the host cells are cultured to expand cells to levels of protein or polypeptide required for screening and/or analysis.

11. The method of claim 1, wherein said method comprises transducing host cells with the pooled-library of baculovirus vectors at a multiplicity of infection (MOI) of 0.1-0.01.

12. The method of claim 1, wherein said method comprises culturing the cells for 2 to 5 days.

13. The method of claim 1, wherein the viral inhibitor is selected from the group consisting of chloroquine, ammonium chloride, and oseltamivir.

14. The method of claim 1, wherein the viral inhibitor is selected from the group consisting of chloroquine and oseltamivir.

15. The method of claim 1, wherein the viral inhibitor is selected from the group consisting of chloroquine and ammonium chloride.

16. The method of claim 1, wherein the viral inhibitor is a neuraminidase inhibitor.

* * * * *